(12) United States Patent
Oe et al.

(10) Patent No.: US 6,541,493 B1
(45) Date of Patent: Apr. 1, 2003

(54) CRYSTALS OF 5-[{6-(2-FLUOROBENZYL)OXY-2-NAPHTHYL}METHYL]-2,4-THIAZOLIDINEDIONE

(75) Inventors: Takayuki Oe, Kanagawa (JP); Hiroaki Ueno, Kanagawa (JP); Akira Maruyama, Ibaraki (JP); Katsuhiko Masuda, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/856,295
(22) PCT Filed: Nov. 19, 1999
(86) PCT No.: PCT/JP99/06492
§ 371 (c)(1), (2), (4) Date: Aug. 20, 2001
(87) PCT Pub. No.: WO00/31055
PCT Pub. Date: Jun. 2, 2000

(30) Foreign Application Priority Data

Nov. 19, 1999 (JP) .......... 10-330546

(51) Int. Cl.⁷ .......... C07D 277/34
(52) U.S. Cl. .......... 514/369; 548/183
(58) Field of Search .......... 548/183; 514/369

(56) References Cited

U.S. PATENT DOCUMENTS 5,594,016 A * 1/1997 Ueno .......... 514/369

FOREIGN PATENT DOCUMENTS

| EP | 0 604 983 | 7/1994 |
| JP | 06 247945 | 9/1994 |
| JP | 10-139768 | 5/1998 |

* cited by examiner

*Primary Examiner*—Robert Gerstl
(74) *Attorney, Agent, or Firm*—Wenderoth, Lind & Ponack, L.L.P.

(57) ABSTRACT

The invention relates to type A crystal of 5-[{6-(2-fluorobenzyl)oxy-2-naphthyl}methyl]-2,4-thiazolidinedione characterized to have characteristic absorption peaks (2θ) at 11.5°±0.3°, 14.5°±0.2°, 16.2°±0.3°, 17.0°±0.3°, 17.7°±0.2°, 18.6°±0.3°, 19.1°±0.2°, 21.3°±0.4°, 22.4°±0.5°, 25.7°±0.5° and 28.3°±0.5° in a powder X-ray diffraction pattern, and also to a method for preparation thereof, and a pharmaceutical composition comprising the same. The crystal is excellent in stability, and has advantages in handling, storage, and pharmaceutical preparation. The invention also relates to type B, C and D crystals of said compound.

22 Claims, 12 Drawing Sheets

CRYSTALS OF 5-[{6-(2-FLUOROBENZYL) OXY-2-NAPHTHYL}METHYL]-2,4-THIAZOLIDINEDIONE

This application is a 371 of PCT/JP99/06492 filed Nov. 19, 1999.

FIELD OF THE INVENTION

The present invention relates to a stable and novel type A crystal of 5-[{6-(2-fluorobenzyl)oxy-2-naphthyl}methyl]-2,4-thiazolidinedione (referred to as "MCC-555" in the specification), which is useful as an active ingredient of therapeutic medicaments for diabetes and a complication thereof, hyperlipidemia and a complication thereof and the like.

BACKGROUND OF THE INVENTION

Diabetes is a complicated disease caused by hyperglycemia, and the disease is brought by deficiency of insulin action which reduces blood glucose. Diabetes can be classified into several types based on their pathologic state. Among them, those regarded as important are insulin dependent diabetes (type I diabetes) which requires supplement of insulin because of its deficiency, and non-insulin dependent diabetes (type II diabetes) where insulin fails to effect due to abnormalities of receptors, saccharide transporting carriers and the like, although sufficient amount of insulin is secreted.

In recent years, agents improving insulin resistance have been much interested which reduce blood glucose by improving insulin resistance in peripheral tissues that is a cause of non-insulin dependent diabetes.

Some of the inventors of the present invention achieved an invention relating to 5-[{6-(2-fluorobenzyl)oxy-2-naphthyl}methyl]-2,4-thiazolidinedione, an agent for improving insulin resistance that has excellent hypoglycemic action and hypolipidemic action, and filed patent applications directed to the invention (the Japanese Patent Unexamined Publication (KOKAI) Nos. (Hei) 6-247945/1994 and (Hei) 10-139768/1998). The claims of the Japanese Patent Unexamined Publication (KOKAI) (Hei) 6-247945/1994 are directed to novel naphthalene derivatives including 5-[{6-(2-fluorobenzyl)oxy-2-naphthyl}methyl]-2,4-thiazolidinedione and salts thereof having hypoglycemic and hypolipidemic action, and the claims of the Japanese Patent Unexamined Publication No. (Hei) 10-139768/1998 are directed to an industrial process of manufacture thereof.

The present invention is based on the discovery that a novel crystal form of 5-[{6-(2-fluorobenzyl)oxy-2-naphthyl}methyl]-2,4-thiazolidinedione is apparently superior to other crystal forms. The novel crystal form is herein referred to as "type A crystal," whereas the other crystal forms mentioned herein are referred to as "type B crystal", "type C crystal," and "type D crystal" only for reasons of convenience. The type A crystal has a novel crystal form, and its excellent stability and a manufacturing process thereof have not been known to date. According to the method disclosed in the Japanese Patent Unexamined Publication (KOKAI) No. (Hei) 6-247945/1994, 5-[{6-(2-fluorobenzyl)oxy-2-naphthyl}methyl]-2,4-thiazolidinedione is recrystallized in the presence of a mixed solvent of ethyl acetate and hexane to obtain polymorphic forms of 5-[{6-(2-fluorobenzyl)oxy-2-naphthyl}methyl]-2,4-thiazolidinedione. As a product of the aforementioned method, the type D crystal or a mixture mainly composed of the type D crystal may be obtained depending on various factors such as heating temperature, an amount or a mixing ratio of the solvents and the like, and accordingly, the type A crystal cannot be obtained alone. According to the method of the Japanese Patent Unexamined Publication (KOKAI) No. (Hei) 10-139768/1998, 5-[{6-(2-fluorobenzyl)oxy-2-naphthyl}methyl]-2,4-thiazolidinedione is recrystallized in toluene as a solvent to obtain polymorphic forms of the compound. This method may most frequently yield a product comprising a mixture of the type A and type D crystals with a fluctuating content ratio depending on various factors such as heating temperature, a cooling rate, an amount of the solvent and the like. However, these patent documents are silent about the possibility of the polymorphism, and hence no information about the type A, B, C and D crystals are disclosed therein.

DISCLOSURE OF THE INVENTION

The present invention provides a crystal of 5-[{6-(2-fluorobenzyl)oxy-2-naphthyl}methyl]-2,4-thiazolidinedione distinguishable from the known crystals, which is novel and excellent in stability, and has advantages in handling, storage, and manufacture of pharmaceutical preparation.

The present invention thus provides Type A crystal of 5-[{6-(2-fluorobenzyl)oxy-2-naphthyl}methyl]-2,4-thiazolidinedione characterized to have characteristic absorption peaks (2θ) at 11.5°±0.3° in a powder X-ray diffraction pattern.

According to preferred embodiment of the present invention, there are provided the type A crystal of said compound characterized to have characteristic absorption peaks (2θ) at 11.5°±0.3° and 25.7°±0.5° in a powder X-ray diffraction pattern; The type A crystal of said compound characterized to have characteristic absorption peaks (2θ) at 22.4°±0.5° and 25.7°±0.5° in a powder X-ray diffraction pattern; The type A crystal of said compound characterized to have characteristic absorption peaks (2θ) at 11.5°±0.3° and 22.4°±0.5° in a powder X-ray diffraction pattern; The type A crystal of said compound characterized to have characteristic absorption peaks (2θ) at 11.5°±0.3°, 17.0°±0.3°, 17.7°±0.2°, 22.4°±0.5° and 25.7°±0.5° in a powder X-ray diffraction pattern; and the type A crystal of said compound characterized to have characteristic absorption peaks (2θ) at 11.5°±0.3°, 14.5°±0.2°, 16.2°±0.3°, 17.0°±0.3°, 17.7°±0.2°, 18.6°±0.3°, 19.1°±0.2°, 21.3°±0.4°, 22.4°±0.5°, 25.7°±0.5° and 28.3°±0.5° in a powder X-ray diffraction pattern.

The present invention also provides a method for preparing the aforementioned type A crystal of 5-[{6-(2-fluorobenzyl)oxy-2-naphthyl}methyl]-2,4-thiazolidinedione, which comprises the step of heating and stirring 5-[{6-(2-fluorobenzyl)oxy-2-naphthyl}-methyl]-2,4-thiazolidinedione in an alcoholic solvent, and a pharmaceutical composition comprising the aforementioned type A crystal of 5-[{6-(2-fluorobenzyl)oxy-2-naphthyl}methyl]-2,4-thiazolidinedione and a pharmaceutically acceptable carrier.

Furthermore, the present invention provides type B crystal of 5-[{6-(2-fluorobenzyl)oxy-2-naphthyl}methyl-]-2,4-thiazolidinedione characterized to have characteristic diffraction peaks (2θ) at 10.5°±0.5°, 18.4°±0.5°, 20.9°±0.5°, 23.0°±0.5°, 26.7°±0.5° and 29.2°±0.5° in a powder X-ray diffraction pattern;

type C crystal of said compound characterized to have characteristic diffraction peaks (2θ) at 12.5°±0.5°, 14.5°±0.5°, 17.6°±0.5°, 18.8°±0.5°, 22.1°±0.5°, 25.9°±0.5°, 26.6°±0.5° and 28.3°±0.5° in a powder X-ray diffraction pattern; and type D crystal of said compound characterized to have characteristic diffraction peaks (2θ) at 10.7°±0.2°, 14.5°±0.2°, 15.1°±0.2°, 15.8°±0.2°, 17.4°±0.2°, 18.5°±0.2°, 20.5°±0.2°, 22.2°±0.2°, 25.3°±0.2°, 26.8°±0.2° and 27.8°±0.2° in a powder X-ray diffraction pattern.

BRIEF EXPLANATION OF THE INVENTION

BEST MODE FOR CARRYING OUT THE INVENTION

Figure 1:
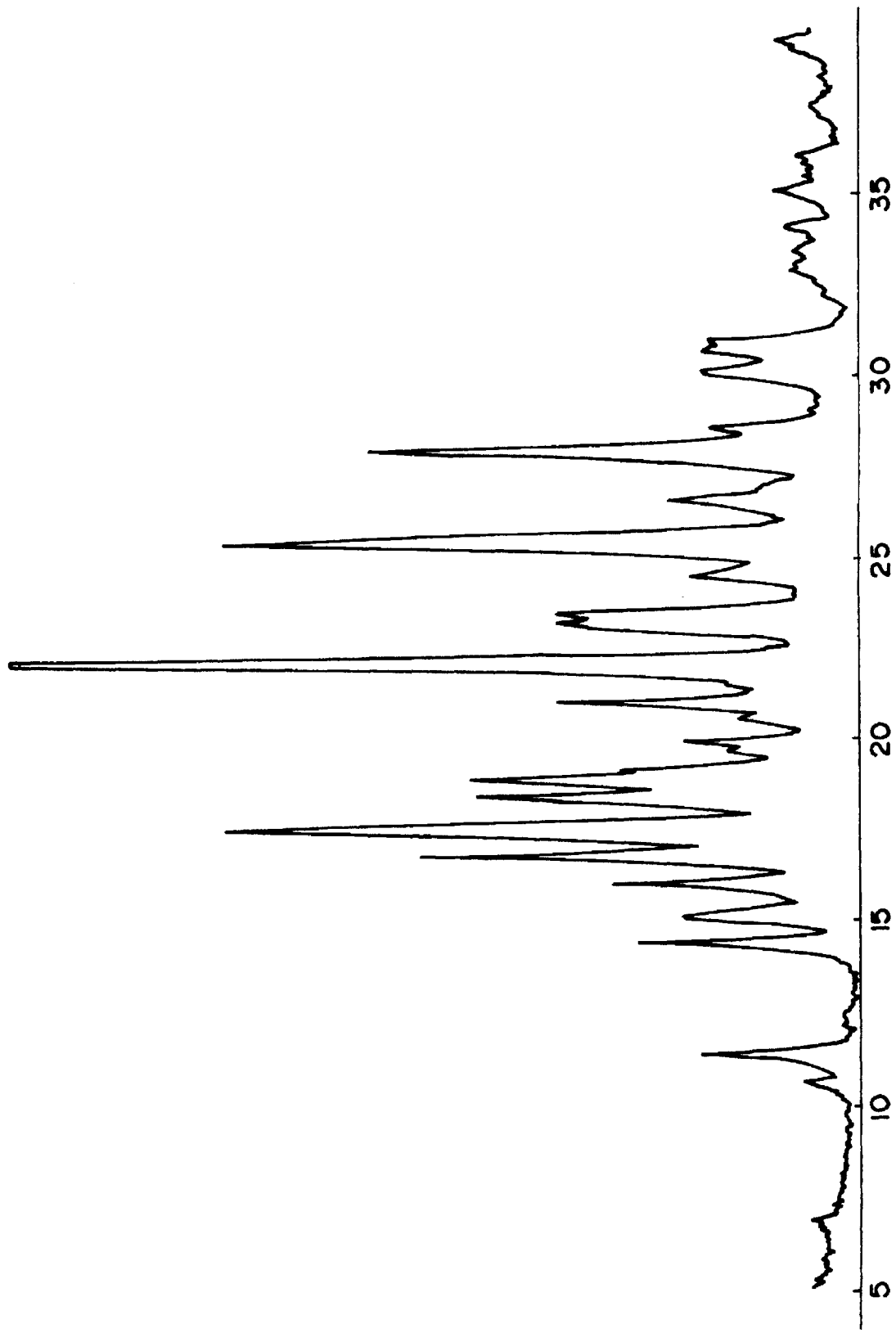
FIG. 1 shows a powder X-ray diffraction pattern of the type A crystal.
Figure 2:
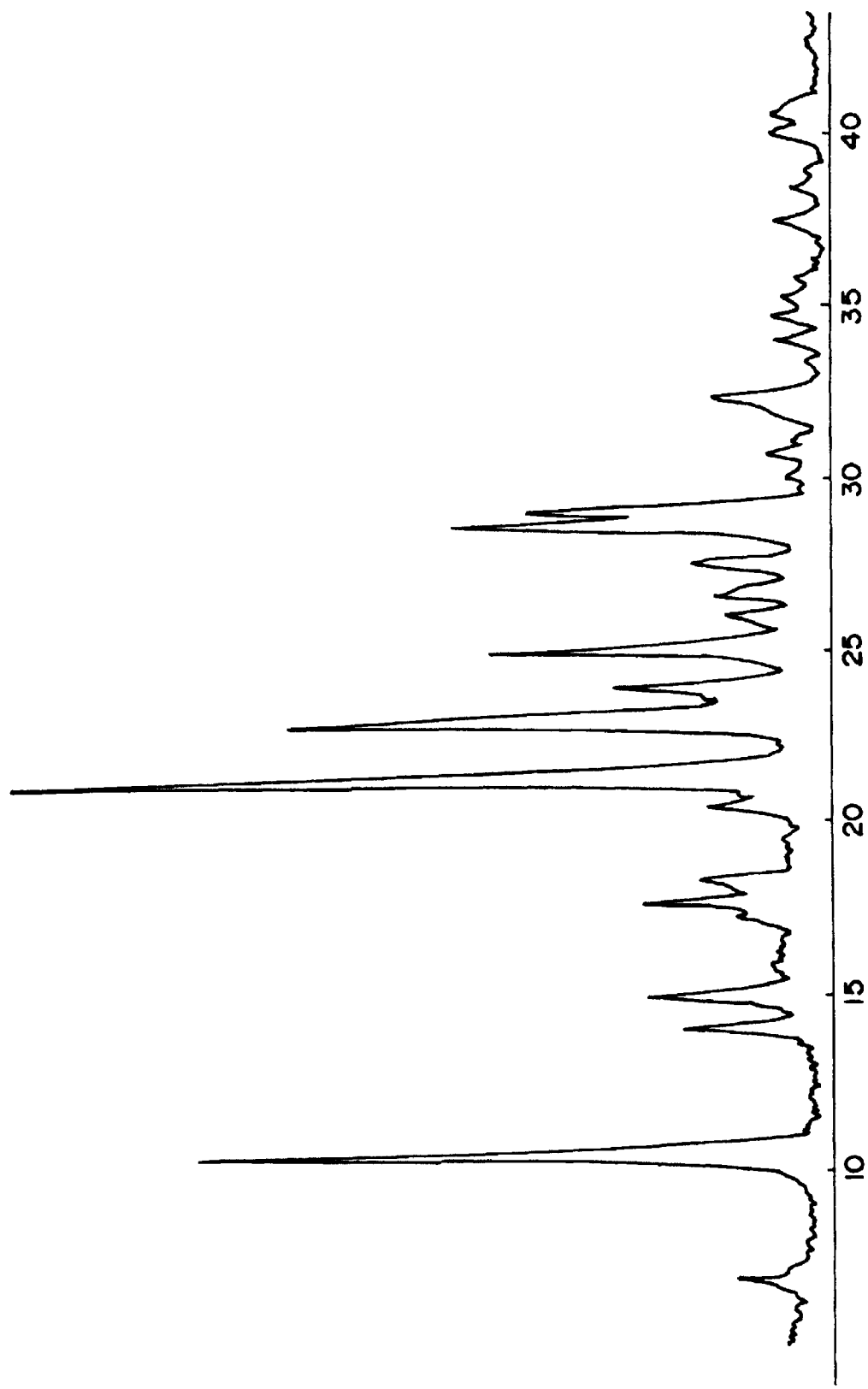
FIG. 2 shows a powder X-ray diffraction pattern of the type B crystal.
Figure 3:
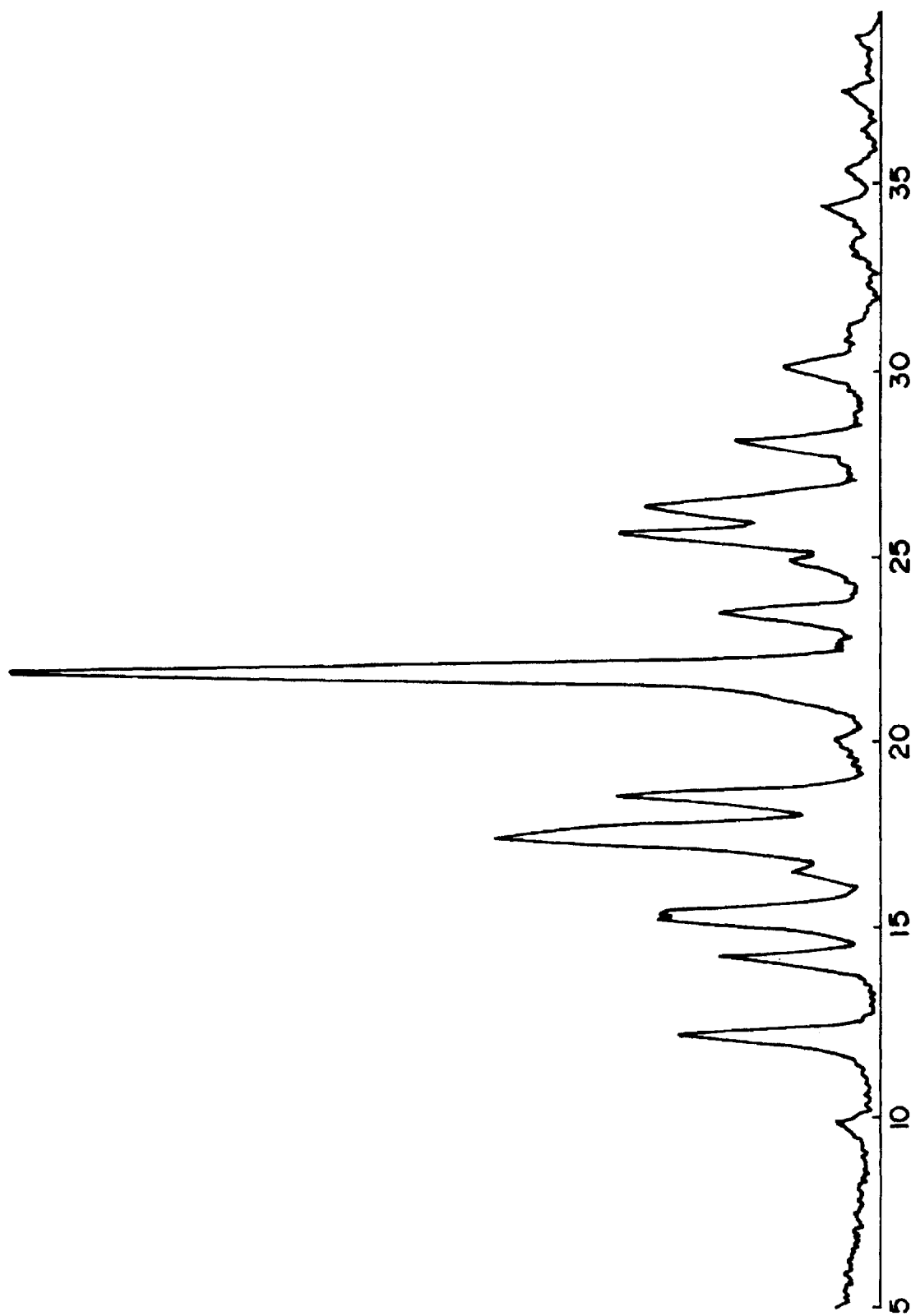
FIG. 3 shows a powder X-ray diffraction pattern of the type C crystal.
Figure 4:
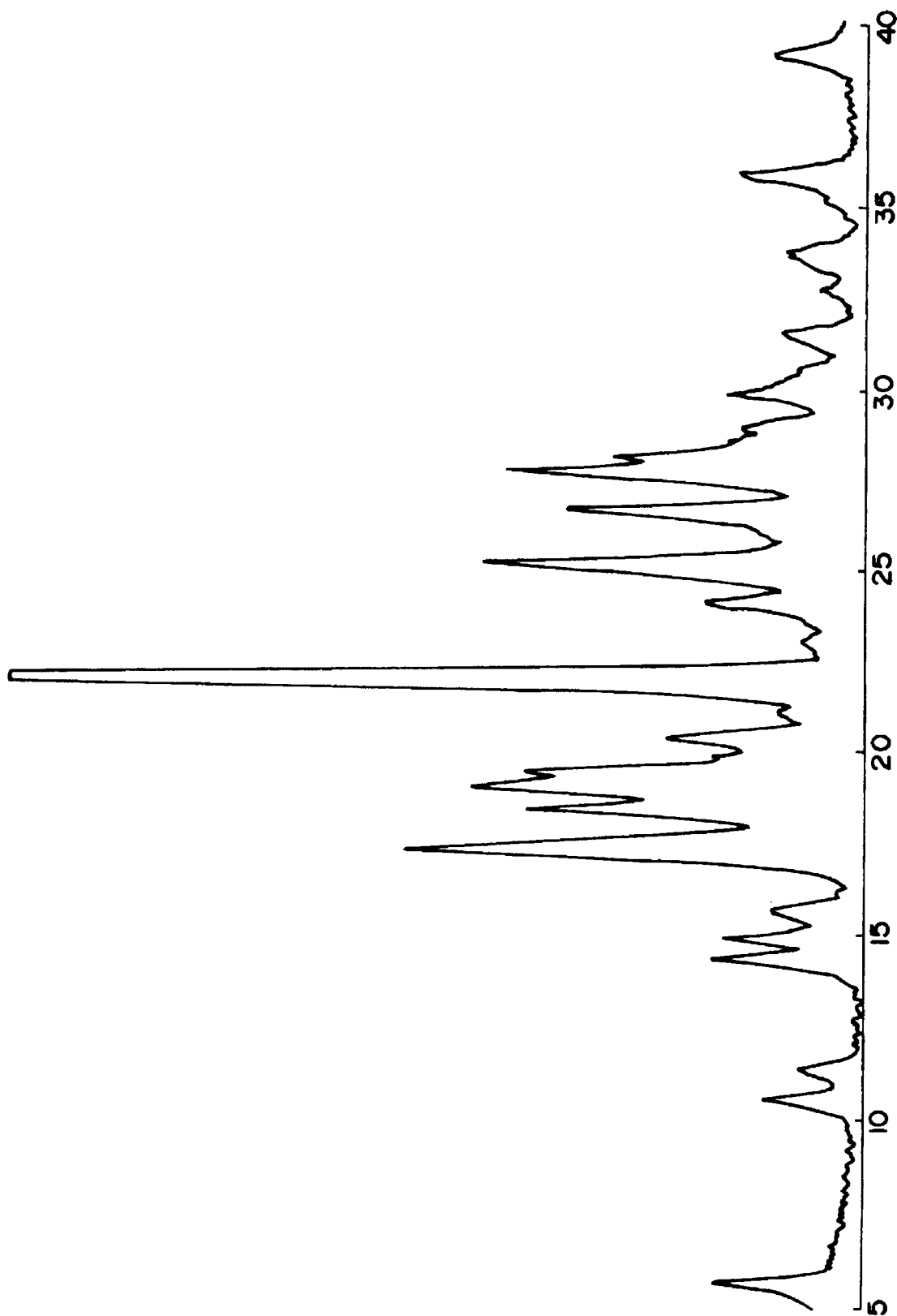
FIG. 4 shows a powder X-ray diffraction pattern of the type D crystal.

The novel type A crystal of 5-[{6-(2-fluorobenzyl)oxy-2-naphthyl}methyl]-2,4-thiazolidinedione of the present invention, i.e., MCC-555, is a crystal of a compound represented by the following chemical formula.

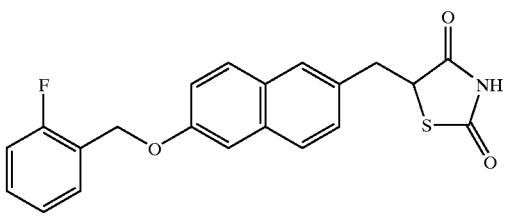

MCC-555 can be obtained by heating and stirring any one of the crystal forms or a mixture thereof, preferably a mixture of polymorphic forms containing the type A crystal, in an alcoholic solvent.

The alcoholic solvent is not particularly limited. Preferred examples include aliphatic alcohols, more preferably aliphatic alcohols having 1 to 4 carbon atoms. More specifically, examples include ethanol, 1-propanol, 2-propanol, 1-butanol, 2-butanol or the like. According to the present invention, ethanol, in particular, anhydrous ethanol can most preferably be used.

The reaction conditions are not particularly limited. The crystal can be easily obtained with good reproducibility by heating and stirring a mixture in a form of a suspension preferably under atmospheric pressure or under pressure and at a temperature within the range of from about 50° C. to refluxing temperature, preferably within the range of from 70 to 85° C.

When any one of the crystal forms or a mixture thereof is heated to a temperature within the optimum temperature range to produce MCC-555, it is preferred that the alcoholic solvent is used in an amount sufficient to achieve at least partial dissolution of 5-[{6-(2-fluorobenzyl)oxy-2-naphthyl}methyl]-2,4-thiazolidinedione. Generally, it is sufficient to use about from 4 to 10 ml of an alcohol per 1 g of any one of the crystal forms of 5-[{6-(2-fluorobenzyl)oxy-2-naphthyl}methyl]-2,4-thiazolidinedione or a mixture thereof; however, a better result may sometimes be obtained by using an increased or decreased amount of an alcohol.

Heating time required for substantially complete formation of MCC-555 according to the aforementioned method may vary from several minutes to about 5 hours or more. An optimum heating time required for an individual process may vary depending on several factors such as temperature, an amount of solvent and the like. When the above process is performed by heating and refluxing ethanol under atmospheric pressure, or by heating at about 78° C. under pressure, a time required for substantially complete formation of the desired type A crystal is generally about 2 to 5 hours. Degree of the formation of MCC-555 can be observed by collecting a sample, cooling the sample to room temperature, isolating precipitates by filtration, and measuring the precipitates by powder X-ray diffractometry. As will be described below, each of the polymorphic forms of 5-[{6-(2-fluorobenzyl)oxy-2-naphthyl}methyl]-2,4-thiazolidinedione provides respective characteristic absorption bands.

When 5-[{6-(2-fluorobenzyl)oxy-2-naphthyl}methyl]-2,4-thiazolidinedione is heated and suspended in ethanol as a solvent, the type D crystal herein defined or a mixture of type A and type D crystals may sometimes be obtained as a product, if a heating temperature is below 78° C., or if a heating time is insufficient, even though the heating is performed at a temperature within the above-mentioned range suitable for the formation of the type A crystal.

The crystal forms of 5-[{6-(2-fluorobenzyl)oxy-2-naphthyl}methyl]-2,4-thiazolidinedione and mixtures thereof can be prepared by the methods described in the Japanese Patent Unexamined Publication Nos. (Hei) 6-247945/1994 and (Hei) 10-139768/1998, or by similar methods.

The type B crystal of 5-[{6-(2-fluorobenzyl)oxy-2-naphthyl}methyl]-2,4-thiazolidinedione can be obtained by recrystallization of any one of the crystal forms or a mixture thereof from an organic solvent, preferably from toluene, at a low temperature, preferably at about 0° C.

The type C crystal can be obtained by recrystallization of one of the crystal forms or a mixture thereof from an organic solvent, preferably 1-propanol or 1-butanol.

The type D crystal can be obtained by recrystallization of one of the crystal forms or a mixture thereof from an organic solvent, preferably a mixed solvent of ethyl acetate and hexane.

Figure 5:
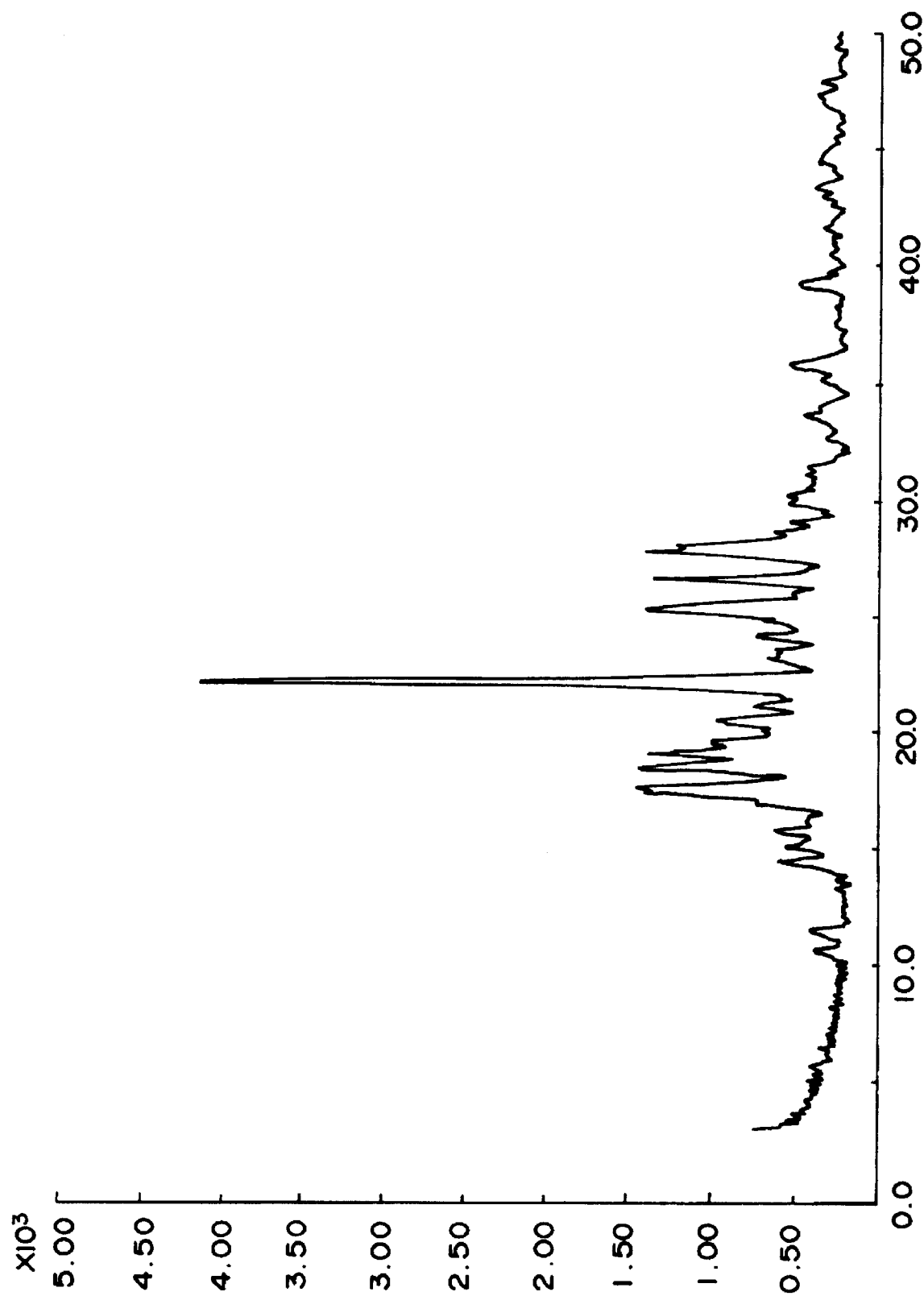
FIG. 5 shows a powder X-ray diffraction pattern of 5-[{6-(2-fluorobenzyl)oxy-2-naphthyl}methyl]-2,4-thiazolidinedione obtained by the method disclosed in Japanese Patent Unexamined Publication (KOKAI) No. (Hei) 6-247945/1994.
Figure 6:
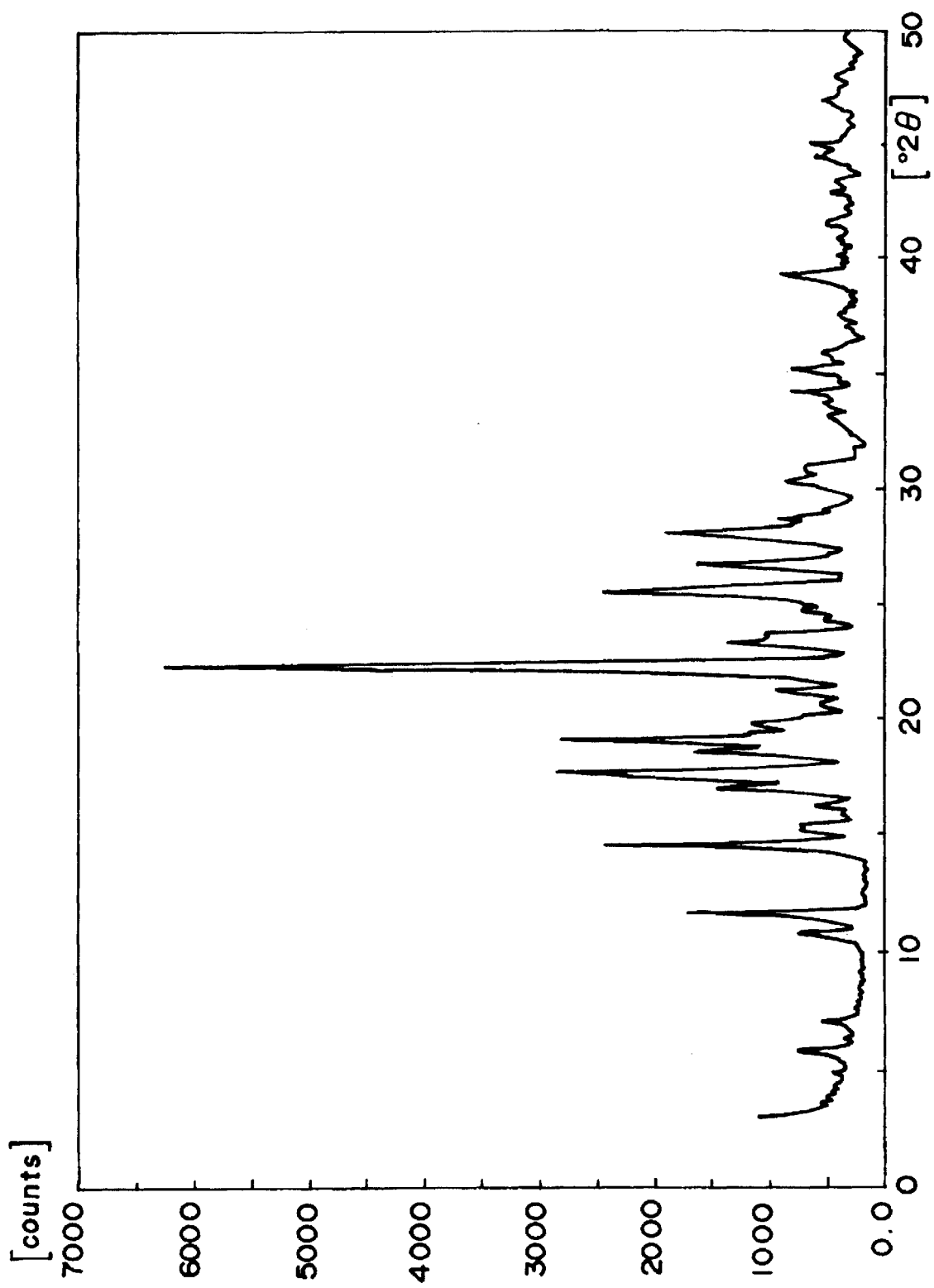
FIG. 6 shows a powder X-ray diffraction pattern of 5-[{6-(2-fluorobenzyl)oxy-2-naphthyl}methyl]-2,4-thiazolidinedione obtained by the method disclosed in Patent Unexamined Publication (KOKAI) No. (Hei) 10-139768/1998.
Figure 7:
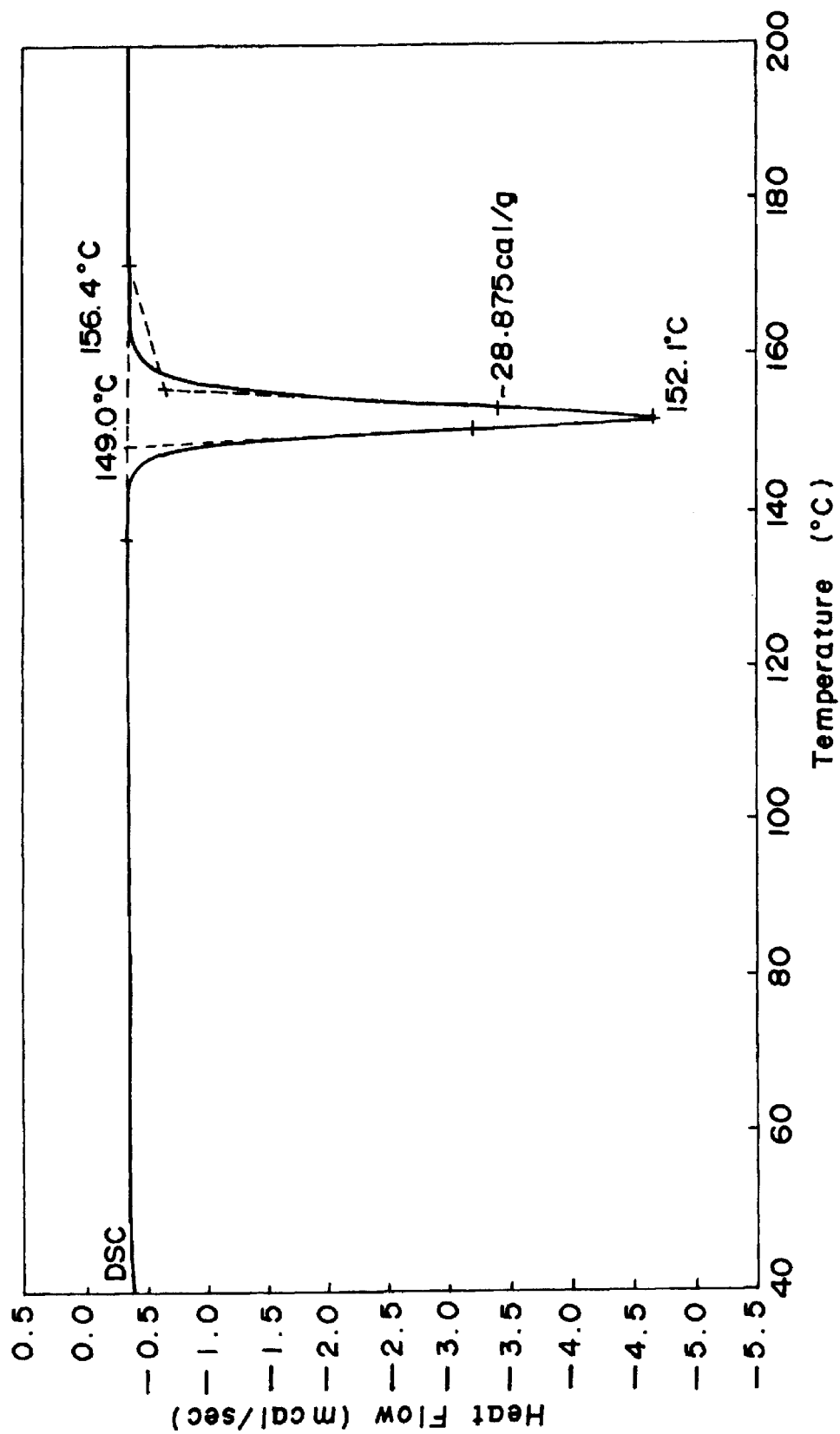
FIG. 7 shows a differential scanning calorimetry pattern of the type A crystal.
Figure 8:
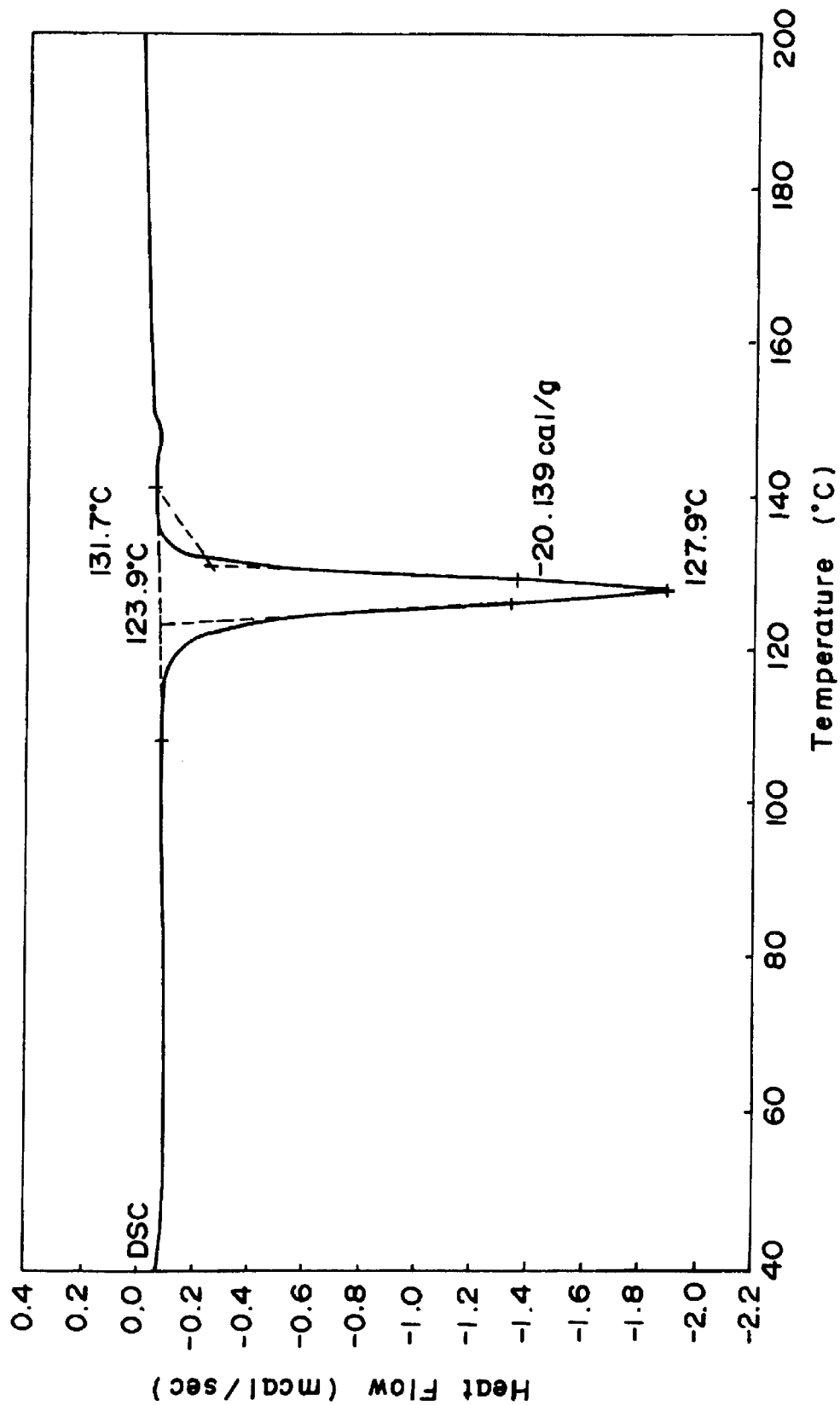
FIG. 8 shows a differential scanning calorimetry pattern of the type B crystal.
Figure 9:
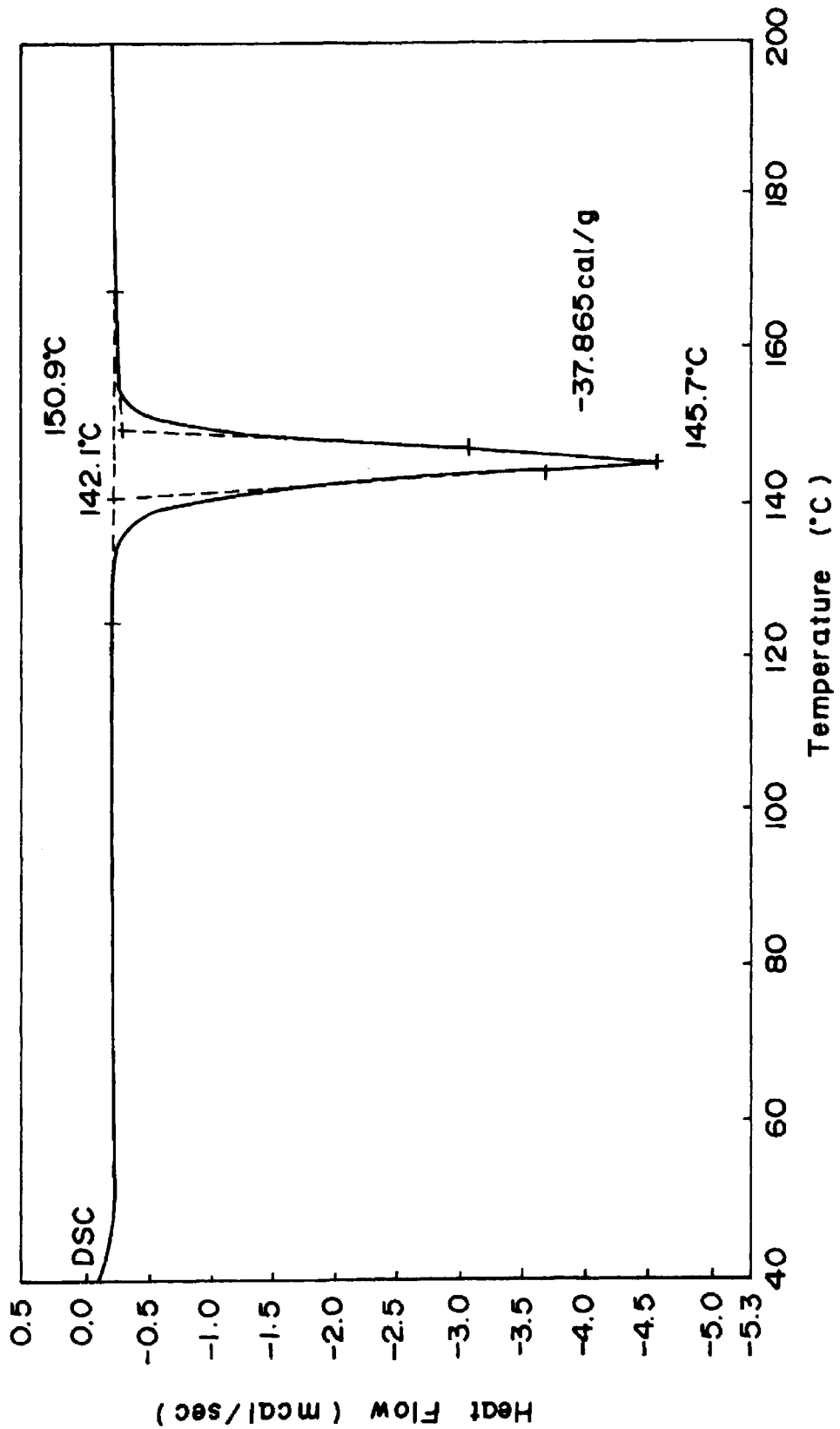
FIG. 9 shows a differential scanning calorimetry pattern of the type C crystal.
Figure 10:
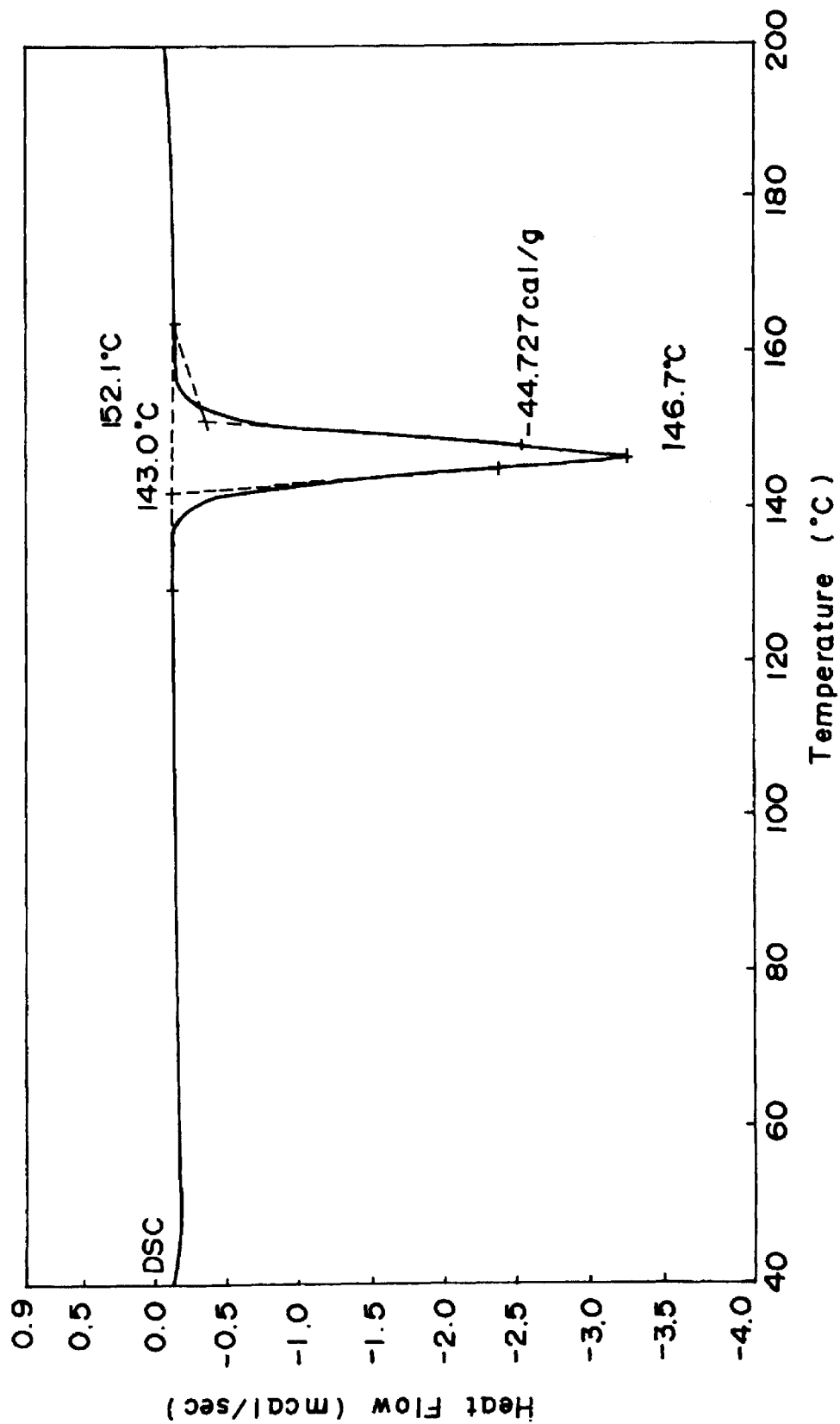
FIG. 10 shows a differential scanning calorimetry pattern of the type D crystal.
Figure 11:
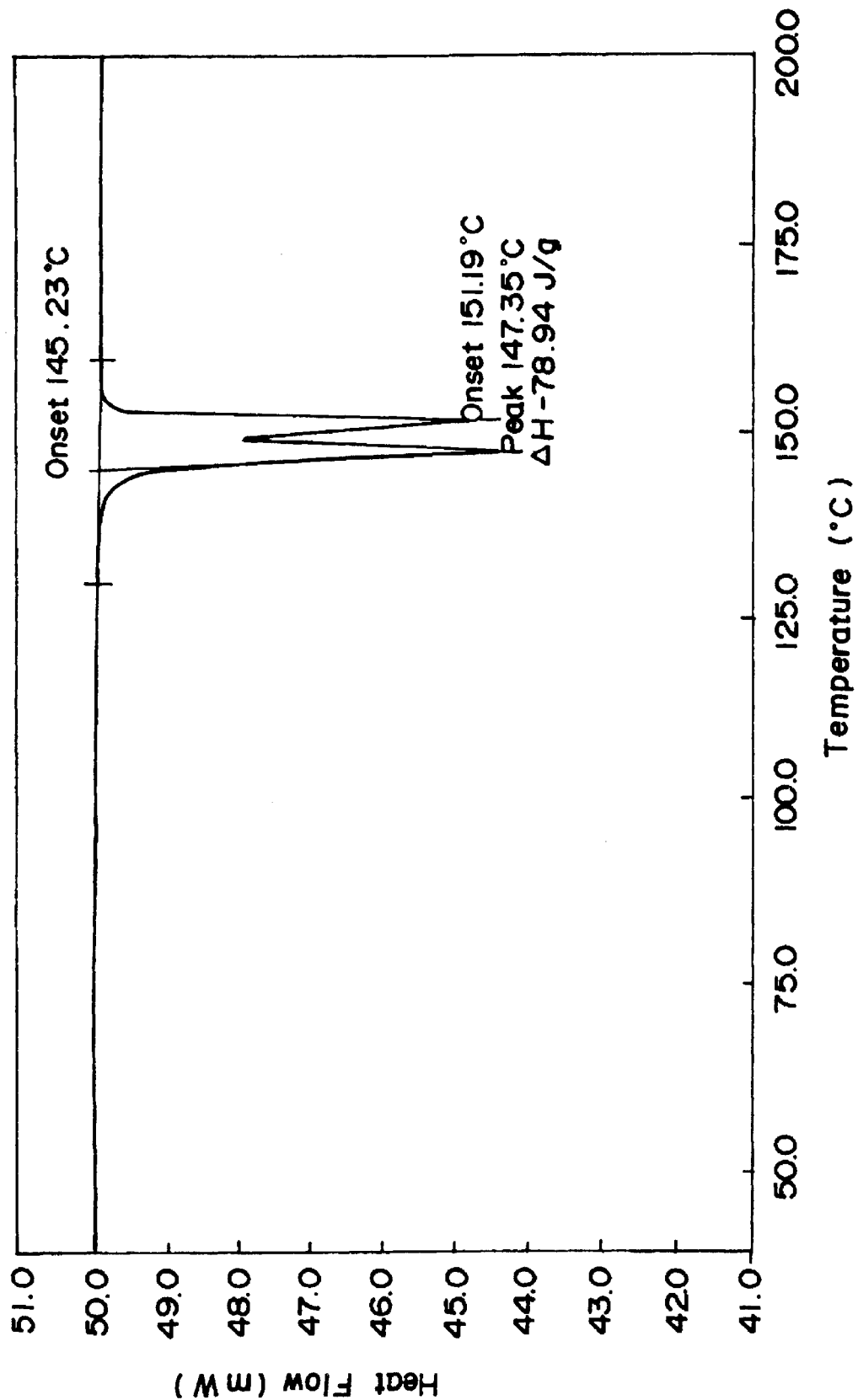
FIG. 11 shows a differential scanning calorimetry pattern of 5-[{6-(2-fluorobenzyl)oxy-2-naphthyl}methyl]-2,4-thiazolidinedione obtained by the method disclosed in Japanese Patent Unexamined Publication (KOKAI) No. (Hei) 6-247945/1994.
Figure 12:
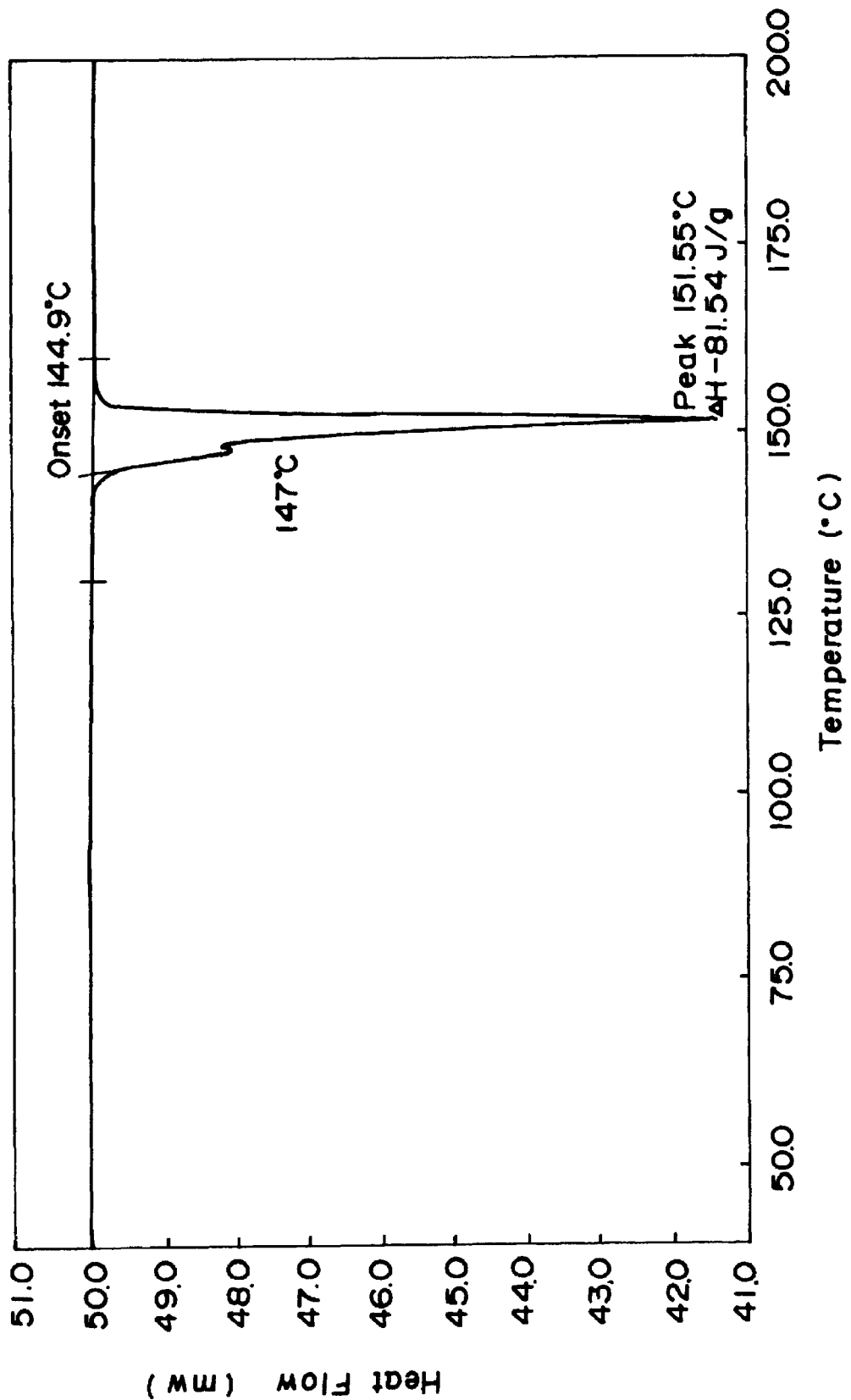
FIG. 12 shows a differential scanning calorimetry pattern of 5-[{6-(2-fluorobenzyl)oxy-2-naphthyl}methyl]-2,4-thiazolidinedione obtained by the method disclosed in Patent Unexamined Publication (KOKAI) No. (Hei) 10-139768/1998.

The polymorphic form obtained by the method disclosed in the Japanese Patent Unexamined Publication No. (Hei) 6-247945/1994 is characterized by the data shown in FIG. 5 and FIG. 11, and the polymorphic form obtained by the method disclosed in the Japanese Patent Unexamined Publication No. (Hei) 10-139768/1998 is characterized by the data shown in FIG. 6 and FIG. 12. By comparing the data shown in these figures with the corresponding data of the type A crystal of the present invention, it can readily be understood that those known substances composed of a mixture are different from the substance of the present invention. For example, there are differences between the crystals obtained by the conventional methods and the crystal of the present invention in powder X-ray diffraction patterns. In addition, there are apparent differences in differential scanning calorimetry patterns as shown in FIGS. 7, 11 and 12, i.e., the type A crystal is characterized by one sharp endothermic peak due to the fusion beginning at about 149° C., whereas both of the crystals obtained by the conventional methods show endothermic property due to the fusion at a lower temperature than that observed in the type A crystal. By comparing the data shown in these figures with the corresponding data of the type B, C and D crystals of the present invention, it can readily be understood that those known substances composed of a mixture are different from the substances of the present invention.

The powder X-ray diffraction data and the differential scanning calorimetry data clearly demonstrate that the substance of the present invention has distinguishable crystal form from the known crystal forms of 5-[{6-(2-fluorobenzyl)oxy-2-naphthyl}methyl]-2,4-thiazolidinedione.

The compound of the present invention has excellent hypoglycemic and hypolipidemic action, and can be used as a medicament. The compound may be added with one or more ordinary carriers and prepared as a pharmaceutical preparation suitable for each route of administration. For example, the preparations for oral administration may be manufactured in the form of tablets, capsules, granules, powders, liquids and other. For the manufacture of solid preparations for oral administration, conventional excipients, binders, lubricants, colorants, disintegrating agents and other can be used. The hypoglycemic and hypolipidemic agent can be used, for example, for the treatment of diabetes and a complication thereof, hyperlipidemia and a complications thereof, hyperuricemia, leukemia, and pancreatitis.

Examples of the excipients include, for example, lactose, starch, talc, magnesium stearate, crystal cellulose, methylcellulose, carboxymethylcellulose, glycerin, sodium alginate, gum Arabic and the like. Examples of the binders include, for example, polyvinyl alcohol, polyvinyl ether, ethylcellulose, gum Arabic, shellac, saccharose and the like. Examples of the lubricants include, for example, magnesium stearate, talc and the like. In addition, commonly used known colorants, disintegrating agents and the like can be suitably used. Tablets may be coated in a well-known manner.

The liquid preparations may be in the form of aqueous or oil suspensions, solutions, syrups, elixirs or other, and such preparations may be manufactured by a conventional method. When an injection is prepared, the compound of the present invention may be added with a pH modifier, a buffering agent, a stabilizer, an isotonicity, a local anesthetic agent and other, and prepared as subcutaneous, intramuscular, or intravenous injections in a conventional manner. As a base material for the manufacture of suppositories, for example, oil and fat bases such as cacao butter, polyethylene glycol, Witepsol (registered trademark of Dynamite Nobel) and other can be used.

Doses of the pharmaceutical preparation produced as described above may vary depending on symptoms, body weight and age of a patient, route of administration and the like, and the same dose may not be always applied. However, in general, the compound of the present invention may preferably be administered in an amount within the range of about 0.01 to 2000 mg per day for an adult, and generally, the dose may preferably be administered once a day or two to four times a day as divided portions.

The type A crystal of the present invention has higher stability compared to the other crystal forms, and is a unique crystal which is kept as the stable form under various conditions in usual handling, storage, manufacturing process of preparations and the like. Accordingly, the medicaments for therapeutic treatment of diabetes and a complication thereof, hyperlipidemia and a complication thereof and the like can be supplied steadily and in large quantity by using the type A crystal of the present invention. Furthermore, the present invention provides the other new crystal forms, the type B, C and D.

EXAMPLES

The present invention will be further explained in detail by referring to examples. However, the scope of the present invention is not limited to these examples.

Reference Example 1

Preparation of a mixture of 5-[{6-(2-fluorobenzyl)oxy-2-naphthyl}methyl]-2,4-thiazolidinedione polymorphic forms 50.0 g of 5-[{6-(2-fluorobenzyl)oxy-2-naphthyl}methyl]-2,4-thiazolidinedione (roughly purified product, prepared by the method described in the Japanese Patent Unexamined Publication No. (Hei) 10-139768/1998), was add to 375 ml of toluene and heated with stirring at refluxing temperature. After the solid was completely dissolved, the solution was cooled to 20° C. with stirring. The reaction mixture was filtered, and the filter cake was washed with toluene and dried under reduced pressure to obtain 48.8 g of a mixture of polymorphic forms comprising the type A and type D crystals of 5-[{6-(2-fluorobenzyl)oxy-2-naphthyl}methyl]-2,4-thiazolidinedione (98% of theoretical yield). Melting point: 149–151° C.

Elemental analysis (as $C_{21}H_{16}FNO_3S$): Calculated (%): C, 66.13; H, 4.23; N, 3.67 Found: C, 66.06; H, 4.08; N, 3.68

Example 1

Preparation of MCC-555 (1)

The mixture of polymorphic forms of the type A and type D crystals obtained in Reference Example 1 (400 mg) was suspended in ethanol (4.0 ml), heated under reflux for one hour with stirring, and then cooled to room temperature with stirring. The reaction mixture was filtered, and the filter cake was washed with ethanol and dried under reduced pressure to obtain 361 mg of MCC-555 as white crystals (90% of theoretical yield). Melting point: 150–152° C.

Example 2

Preparation of MCC-555 (2)

The mixture of polymorphic forms of the type A and type D crystals obtained in Reference Example 1 (15.0 g) was added to ethanol (68 ml) and suspended with heating under pressure in an autoclave at 78° C. for 3 hours. Then, the mixture was cooled to room temperature and further stirred for 1 hour. The reaction mixture was filtered, and the filter cake was washed with ethanol and dried under reduced pressure to obtain 14.6 g of MCC-555 as white crystals (97% of theoretical yield). Melting point: 150–152° C.

Example 3

Preparation of Type B Crystal

The mixture of polymorphic forms of the type A and type D crystals obtained in Reference Example 1 (1.62 g) was added to toluene (250 ml) and heated to about 65° C. with stirring. After the crystals were completely dissolved, the solution was slowly cooled to about 0° C. with stirring. The reaction mixture was filtered, and the filter cake was dried under reduced pressure at room temperature to obtain 0.94 g of type B crystals as white crystals (58% of theoretical yield). Melting point: 148–150° C.

Example 4

Preparation of Type C Crystal

The mixture of polymorphic forms of the type A and type D crystals obtained in Reference Example 1 (300 mg) was added to 1-propanol (2.0 ml) and heated at refluxing temperature with stirring. After the crystals were completely dissolved, the solution was slowly cooled to room temperature with stirring. The reaction mixture was filtered, and the filter cake was washed with 1-propanol, and dried under reduced pressure to obtain 281 mg of type C crystals as white crystals (94% of theoretical yield). Melting point: 144–146° C.

Example 5

Preparation of Type D Crystal 7.0 g of 5-[{6-(2-fluorobenzyl)oxy-2-naphthyl}methyl]-2,4-thiazolidinedione (semi-purified product) was add to a mixed solvent of 100 ml of ethyl acetate and 80 ml of hexane, and then heated with stirring at refluxing temperature. After the solid material was completely dissolved, the solution was cooled to room temperature with stirring. The reaction mixture was filtered, and the filter cake was washed with hexane and dried under reduced pressure to obtain 5.4 g of type D crystals as white crystals (77% of theoretical yield). Melting point: 145–147° C.

Elemental analysis (as $C_{21}H_{16}FNO3S$): Calculated (%): C, 66.13; H, 4.23; N, 3.67 Found: C, 66.35; H, 4.20; N, 3.63

Example 6

Preparation of Single Crystal of Type A

The type A crystal obtained in Example 1 or Example 2 (2.6 g) was added with toluene (50.5 g), and the mixture was heated at 100° C. with gentle stirring. The mixture was then cooled to 90° C. all cooling rate of 2° C./min, and the solvent was gently evaporated under reduced pressure at 300 mmHg. After the evaporation to dryness, the residue was cooled to 30° C. at cooling rate of 2° C./min and then allowed to stand for cooling at room temperature to obtain a transparent and colorless single crystal of 0.21 mm×0.066 mm×0.027mm. The intensity of the resulting single crystal was measured by X-ray two-dimensional diffractmeter SMART 1000 using MoK α (5 kV, 40 mA) at −170° C., and then the structure was characterized according to the direct method by conducting the high precision structure analysis based on the full-matrix method of least squares.

Crystallographic Data
Lattice Constant
   a 15.843(2) Å
   b 18.380(3) Å
   c 6.0002(9) Å
   α 91.576(3)°
   β 95.776(1)°
   γ 84.764(4)°
   Volume: 1730.9(4) Å$^3$
   Space Group: P1
   Z: 4
   Dx: 1.464 g/cm$^3$ On the basis of the crystal structure, the powder pattern was simulated to confirm that the resulting single crystal was the type A crystal.

Example 7

Preparation of Single Crystal of Type B

The powder of the type A crystal obtained in Example 1 or Example 2 was add to a mixed solvent of 500 μl of toluene, 200 μl of ethanol and 100 μl of methanol and the mixture was left stand at room temperature for about three months to obtain a transparent and colorless single crystal of 0.3 mm×0.3 mm×0.05 mm. The intensity of the resulting single crystal was measured by X-ray four-axes diffractmeter ENRAF-Nonius CAD4 (ENRAF-Nonius) using CuK α (40 kV, 80 mA), and then the structure was characterized according to the direct method by conducting the high precision structure analysis based on the full-matrix method of least squares.

Crystallographic Data
Lattice Constant
   a 11.158(3) Å
   b 6.586(1) Å
   c 49.243(5) Å
   β 93.85(1)°
   Volume:3610.5(12) Å$^3$
   Space Group: P21/n
   Z: 8
   Dx: 1.403 g/cm$^3$ On the basis of the crystal structure, the powder pattern was simulated to confirm that the resulting single crystal was the type B crystal.

Example 8

Preparation of Single Crystal of Type D

The powder of the type A crystal obtained in Example 1 or Example 2 was add to a mixed solvent of 300 μl of methanol, 100 μl of ethanol and 400 μl of acetonitrile and the mixture was left stand at room temperature for about five days to obtain a transparent and colorless single crystal of 0.3 mm×0.05 mm×0.02 mm. The intensity of the resulting single crystal was measured by X-ray four-axes diffractmeter ENRAF-Nonius CAD4 (ENRAF-Nonius) using CuK α (40 kV, 80 mA), and then the structure was characterized according to the direct method by conducting the high precision structure analysis based on the full-matrix method of least squares.

Crystallographic Data

Lattice Constant a 18.458(2) Å
b 5.9879(3) Å
c 17.819(2) Å
β 115.94 (1)°

Volume: 1771.0 (3) Å$^3$

Space Group: P21/n

Z: 4

Dx: 1.427 g/cm$^3$

On the basis of the crystal structure, the powder pattern was simulated to confirm that the resultant single crystal was that of the type D crystal.

Test Example 1

Characteristics of Various Crystal Forms (1) Powder X-ray Diffraction Analysis

Powder X-ray diffraction patterns of the four polymorphic forms of 5-[{6-(2-fluorobenzyl)oxy-2-naphthyl}methyl]-2,4-thiazolidinedione, i.e., the types A, B, C, and D, were determined by an X-ray diffractometer PW-1700 or PW-1710 (Philips).

The powder X-ray diffraction patterns of the polymorphic forms are shown in FIGS. 1 to 4. Characteristic peaks of the crystal forms are summarized in Table 1.

TABLE 1

| Crystal form | Characteristic peak (2θ) |
| --- | --- |
| A | Sharp peaks at 11.4°, 16.9°, 17.6°, 22.3° and 25.5° |
| B | Sharp peaks at 10.2°, 21.0°, 22.7° and 29.0° |
| C | Sharp peaks at 12.2°, 14.3°, 17.5° and 22.0° |
| D | Sharp peaks at 10.6°, 17.4°, 22.1° and 25.2° |

As clearly seen from these powder X-ray diffraction patterns, 5-[{6-(2-fluorobenzyl)oxy-2-naphthyl}methyl]-2,4-thiazolidinedione exist as the four polymorphic forms which provide different diffraction patterns.

The powder X-ray analyses of the four distinguishable crystals, i.e., the type A to D crystals, were repeated several times. As a result, slight experimental deviation of 2θ values of the characteristic peaks was observed in every determinations, mainly attributable to differences in the preferred orientation of test samples. Accordingly, in the appended claims and the specification, the characteristic peaks are defined as values indicating the median of the dispersed 2θ values of the characteristic peaks together with the range of dispersion. It should thus be noted that medians of the characteristic peaks defined in the claims and the specification are not necessarily identical to the values of characteristic peaks shown in Table 1.

(2) Differential Scanning Calorimetry Analysis (DSC)

A sample (1–3 mg) was placed on a differential scanning calorimetry meter DSC-7 (Perkin-Elmer), or TAS-200 (RIGAKU CORPORATION), and measurement was performed by heating at; a rate of 20° C./minute.

The results obtained are shown in FIGS. 7 to 10 and Table 2.

TABLE 2

| Crystal form | Characteristic |
| --- | --- |
| A | Sharp endothermic band with a peak at 152° C. |
| B | Sharp endothermic band with a peak at 128° C. |
| C | Sharp endothermic band with a peak at 146° C. |
| D | Sharp endothermic band with a peak at 147° C. |

Each crystal form gave apparently distinguishable endothermic peak, and the differences of the polymorphic forms were also verified by this analysis.

(3) Microscopic Observation

Crystal shapes of the type A to D crystals were examined under an optical microscope. As a result, it was found that the type A and type D crystals were needles, and type A crystal was relatively larger. It was also found that the type B and type C crystals were composed of massive crystals in variety of sizes. Differences in shape were also clearly recognized among the crystal forms.

Test Example 2

Stability of the Plural Crystal Forms (1) Change of a Crystal Form by Fusion-solidification A sample (1 to 3 mg) of each of the type A–D crystals was placed on a differential scanning calorimetry meter TAS-200 (RIGAKU CORPORATION), and fused by heating at a rate of 10° C./minute up to a temperature where the crystals were completely fused. Then, the sample was immediately cooled to allow re-solidification. The resulting crystal forms are shown in Table 3.

TABLE 3

| Crystal form before the test | Crystal form after the test |
| --- | --- |
| A | A |
| B | A |
| C | A |
| D | A |

Each of the different crystal forms, i.e., types A to D, gave type A crystals after the fusion in these experiments. The results demonstrate that the type A crystal has higher thermal stability compared to the other crystals.

(2) Stability to Physical Impact

A sample (1 g) of each of the type A–D crystals was placed in an agate mortar, and ground for 1 minute, and powder X-ray diffraction pattern of the ground sample was determined. The pattern was compared with that of the crystal form before the grinding to examine a change of the crystal form. The results are shown in Table 4.

TABLE 4

| Crystal form | Change after grinding |
| --- | --- |
| A | No change |
| B | Partially changed |

TABLE 4-continued

| Crystal form | Change after grinding |
| --- | --- |
| C | No change |
| D | Partially changed |

Partial changes due to impact by the grinding were observed in the crystals of types B and D. Whereas, the crystals of types A and C gave no change, which revealed their stability to physical impact.

(3) Thermal Stability

A sample (about 50 mg) of each of the crystals of types A, C and D was placed in a transparent glass bottle, and heated under atmosphere in an oven at 70° C. for 24 hours. After cooling, powder X-ray diffraction pattern was measured to examine a change of the crystal form. As a result, partial change of the crystal form was observed in the type C crystals, whereas the type A and D crystals gave no change in the crystal forms and were found to have excellent thermal stability.

(4) Stability in a Solvent

The type A crystals were heated with stirring in a state of suspension in a variety of solvents including water, methylene chloride, hexane, ethyl acetate-hexane and ethanol, and then examined the absence or presence of a change of the crystal form after the treatment. As a result, no change was observed in the type A crystals before and after the treatment.

INDUSTRIAL APPLICABILITY

The results of the above studies on the plural crystal forms of 5-[{6-(2-fluorobenzyl)oxy-2-naphthyl}methyl]-2,4-thiazolidinedione demonstrate that the type A crystals has apparently higher stability compared to the other crystals. The type A crystal is the only crystal form which is stable under the various conditions in usual handling, storage and manufacturing process of preparations. Furthermore, the crystal can be easily prepared with good reproducibility according to the method described herein.

What is claimed is:

1. Substantially pure type A crystals of 5-[{6-(2-fluorobenzyl)oxy-2-naphthyl}methyl]-2,4-thiazolidinedione having characteristic absorption peaks (2θ) at 11.5°±0.3°, 17.0°±0.3°, 17.7°±0.2°, 22.4°±0.5° and 25.7°±0.5° in a powder X-ray diffraction pattern.

2. Substantially pure type A crystals of 5-[{6-(2-fluorobenzyl)oxy-2-naphthyl}methyl]-2,4-thiazolidinedione having characteristic absorption peaks (2θ) at 11.5°±0.3°, 14.5°±0.2°, 16.2°±0.3°, 17.0°±0.3°, 17.7°±0.2°, 18.6°±0.3°, 19.1°±0.2°, 21.3°±0.4°, 22.4°±0.5°, 25.7°±0.5° and 28.3°±0.5° in a powder X-ray diffraction pattern.

3. A pharmaceutical composition consisting essentially of type A crystals of 5-[{6-(2-fluorobenzyl)oxy-2-naphthyl}methyl]-2,4-thiazolidinedione having characteristic absorption peaks (2θ) at 11.5°±0.3°, 17.0°±0.3°, 17.7°±0.2°, 22.4°±0.5° and 25.7°±0.5° in a powder X-ray diffraction pattern and a pharmaceutically acceptable carrier.

4. The pharmaceutical composition according to claim 3 which is used for therapeutic treatment of diabetes and a complication thereof, hyperlipidemia and a complication thereof, hyperuricemia, leukemia, and pancreatitis.

5. A pharmaceutical composition consisting of type A crystals of 5-[{6-(2-fluorobenzyl)oxy-2-naphthyl}methyl]-2,4-thiazolidinedione having characteristic absorption peaks (2θ) at 11.5°±0.3°, 17.0°±0.3°, 17.7°±0.2°, 22.4°±0.5° and 25.7°±0.5° in a powder X-ray diffraction pattern and a pharmaceutically acceptable carrier.

6. A method for preparing a type A crystal of 5-[{6-(2-fluorobenzyl)oxy-2-naphthyl}methyl]-2,4-thiazolidinedione according to claim 1, which comprises a step of heating and stirring 5-[{6-(2-fluorobenzyl)oxy-2-naphthyl}methyl]-2,4-thiazolidinedione in ethanol.

7. The method according to claim 6, wherein the heating and stirring are carried out under atmospheric pressure or under pressure.

8. The method according to claim 6, wherein the heating and stirring are carried out at a temperature within the range of about 50° C. to refluxing temperature.

9. Type B crystal of 5-[{6-(2-fluorobenzyl)oxy-2-naphthyl}methyl]-2,4-thiazolidinedione having characteristic diffraction peaks (2θ) at 10.5°±0.5°, 20.9°±0.5°, 23.0°±0.5° and 29.2°±0.5° in a powder X-ray diffraction pattern.

10. Type B crystal of 5-[{6-(2-fluorobenzyl)oxy-2-naphthyl}methyl]-2,4-thiazolidinedione having characteristic diffraction peaks (2θ) at 10.5°±0.5°, 18.4°±0.5°, 20.9°±0.5°, 23.0°±0.5°, 26.7°±0.5° and 29.2°±0.5° in a powder X-ray diffraction pattern.

11. Substantially pure type B crystals having characteristic diffraction peaks (2θ) at 10.5°±0.5°, 20.9°±0.5°, 23.0°±0.5° and 29.2°±0.5° in a powder X-ray diffraction pattern.

12. A composition consisting essentially of type B crystals of 5-[{6-(2-fluorobenzyl)oxy-2-naphthyl}methyl]-2,4-thiazolidinedione having characteristic diffraction peaks (2θ) at 10.5°±0.5°, 20.9°±0.5°, 23.0°±0.5° in a powder X-ray diffraction pattern and a pharmaceutically acceptable carrier.

13. A composition consisting of type B crystals of 5-[{6-(2-fluorobenzyl)oxy-2-naphthyl}methyl]-2,4-thiazolidinedione having characteristic diffraction peaks (2θ) at 10.5°±0.5°, 20.9°±0.5°, 23.0°±0.5° and 29.2°±0.5° in a powder X-ray diffraction pattern and a pharmaceutically acceptable carrier.

14. Type C crystal of 5-[{6-(2-fluorobenzyl)oxy-2-naphthyl}methyl]-2,4-thiazolidinedione having characteristic diffraction peaks (2θ) at 12.5°±0.5°, 14.5°±0.5°, 17.6°±0.5° and 22.1°±0.5° in a powder X-ray diffraction pattern.

15. Type C crystal of 5-[{6-(2-fluorobenzyl)oxy-2-naphthyl}methyl]-2,4-thiazolidinedione having characteristic diffraction peaks (2θ) at 12.5°±0.5°, 14.5°±0.5°, 17.6°±0.5°, 18.8°±0.5°, 22.1°±0.5°, 25.9°±0.5°, 26.6°±0.5° and 28.3°±0.5° in a powder X-ray diffraction pattern.

16. Substantially pure type C crystals of 5-[{6-(2-fluorobenzyl)oxy-2-naphthyl}methyl]-2,4-thiazolidinedione having characteristic diffraction peaks (2θ) at 12.5°±0.5°, 14.5°±0.5°, 17.6°±0.5° and 22.1°±0.5° in a powder X-ray diffraction pattern.

17. A composition consisting essentially of type C crystals of 5-[{6-(2-fluorobenzyl)oxy-2-naphthyl}methyl]-2,4-thiazolidinedione having characteristic diffraction peaks (2θ) at 12.5°±0.5°, 14.5°±0.5°, 17.6°±0.5° and 22.1°±0.5° in a powder X-ray diffraction pattern and a pharmaceutically acceptable carrier.

18. A composition consisting of type C crystals of 5-[{6-(2-fluorobenzyl)oxy-2-naphthyl}methyl]-2,4-thiazolidinedione having characteristic diffraction peaks (2θ) at 12.5°±0.5°, 14.5°±0.5°, 17.6°±0.5° and 22.1°±0.5° in a powder X-ray diffraction pattern and a pharmaceutically acceptable carrier.

19. Substantially pure type D crystals of 5-[{6-(2-fluorobenzyl)oxy-2-naphthyl}methyl]-2,4-thiazolidinedione having characteristic diffraction peaks (2θ) at 10.7°±0.2°, 17.4°±0.2°, 22.2°±0.2° and 25.3°±0.2° in a powder X-ray diffraction pattern.

20. Substantially pure type D crystals of 5-[{6-(2-fluorobenzyl)oxy-2-naphthyl}methyl]-2,4-thiazolidinedione having characteristic diffraction peaks (2θ) at 10.7°±0.2°, 14.5°±0.2°, 15.1°±0.2°, 15.8°±0.2°, 17.4°±0.2°, 18.5°±0.2°, 20.5°±0.2°, 22.2°±0.2°, 25.3°±0.2°, 26.8°±0.2° and 27.8°±0.2° in a powder X-ray diffraction pattern.

21. A composition consisting essentially of type D crystals of 5-[{6-(2-fluorobenzyl)oxy-2-naphthyl}methyl]-2,4-thiazolidinedione having characteristic diffraction peaks (2θ) at 10.7°±0.2°, 17.4°±0.2°, 22.2°±0.2° and 25.3°±0.2° in a powder X-ray diffraction pattern and a pharmaceutically acceptable carrier.

22. A composition consisting of type D crystals of 5-[{6-(2-fluorobenzyl)oxy-2-naphthyl}methyl]-2,4-thiazolidinedione having characteristic diffraction peaks (2θ) at 10.7°±0.2°, 17.4°±0.2°, 22.2°±0.2° and 25.3°±0.2° in a powder X-ray diffraction pattern and a pharmaceutically acceptable carrier.

* * * * *